(12) United States Patent
Yugawa et al.

(10) Patent No.: US 6,656,702 B1
(45) Date of Patent: Dec. 2, 2003

(54) BIOSENSOR CONTAINING GLUCOSE DEHYDROGENASE

(75) Inventors: Keiko Yugawa, Nara (JP); Toshihiko Yoshioka, Hirakata (JP); Shiro Nankai, Hirakata (JP)

(73) Assignee: Matsushita Electric Industrial Co., Ltd., Osaka-fu (JP)

( * ) Notice: Subject to any disclaimer, the term of this patent is extended or adjusted under 35 U.S.C. 154(b) by 0 days.

(21) Appl. No.: 09/345,676

(22) Filed: Jun. 30, 1999

(30) Foreign Application Priority Data

Jul. 3, 1998 (JP) .......................... 10-188799

(51) Int. Cl.⁷ .............................. C12Q 1/32
(52) U.S. Cl. ...................... 435/26; 205/777.5
(58) Field of Search .................. 435/287.9, 287.1, 435/14, 26, 188, 963; 205/777.5; 204/403

(56) References Cited

U.S. PATENT DOCUMENTS

| | | | |
|---|---|---|---|
| 5,236,567 A | * | 8/1993 | Nanba et al. |
| 5,288,636 A | * | 2/1994 | Pollmann et al. |
| 5,997,817 A | * | 12/1999 | Crismore et al. |
| 6,270,637 B1 | * | 8/2001 | Crismore et al. |

FOREIGN PATENT DOCUMENTS

| | | | |
|---|---|---|---|
| EP | 0 560 336 A1 | | 9/1993 |
| EP | 0 795 601 A2 | * | 9/1997 |
| EP | 0 856 586 A1 | | 8/1998 |
| EP | 0 884 392 A1 | | 12/1998 |
| JP | 01 289495 A | | 11/1989 |

OTHER PUBLICATIONS

Derwent abstract of JP 05087767 A (Acc. No. 1993–149757), 1993. Biosensor of long sensor life and prevented deactivation of biological substance.*

Sprules et al. (1996). A disposable reagentless screen-printed amperometric biosensor for the measurement of alcohol in beverages. Analytica Chimica Acta 329(3), pp. 215–221.*

Koji Sode* and Nozomu Yasutake, "Preparation of lyophilized pyrroloquinoline quinone glucose dehydrogenase using trehalose as an additive", Biotechnology Techniques, vol. 11, No. 8, Aug. 1997, pp. 577–580.

Sprules, S.D. et al.: "A disposable reagentless screen-printed amperometric biosensor for the measurement of alcohol in beverages", Analytica Chimica Acta, vol. 329, No. 3, pp. 215–221 (Mar., 1996).

* cited by examiner

*Primary Examiner*—Ralph Gitomer
(74) *Attorney, Agent, or Firm*—Akin, Gump, Strauss, Hauer & Feld, L.L.P.

(57) ABSTRACT

A biosensor that enables rapid and simple quantitation of a substrate with high accuracy and demonstrates an excellent preservation characteristic by best retaining enzyme activity is disclosed. The biosensor comprises an electrically insulating base plate, an electrode system including at least a working electrode and a counter electrode formed on the base plate, and a reaction layer containing at least an enzyme and a sugar. The reaction layer may be formed on the electrode system. The enzyme may be selected from glucose oxidase, glucose dehydrogenase, and fructose dehydrogenase. The sugar is trehalose, sucrose, glycerol, mannitol, and ribose. If the enzyme selected is glucose dehydrogenase whose coenzyme is pyrrolo-quinoline quinone, the use of trehalose is preferable.

4 Claims, 4 Drawing Sheets

BIOSENSOR CONTAINING GLUCOSE DEHYDROGENASE

This application claims benefit to Japan HEI 10-188799 filed Jul. 3, 1998.

BACKGROUND OF THE INVENTION

The present invention relates to a biosensor which facilitates simple and rapid quantitation of a specific component contained in a sample with high accuracy.

Conventionally, various biosensors have been proposed as the system to enable simple quantitation of a specific component contained in a sample without the need of dilution or agitation of a sample solution. The following is a known example of such biosensor (Japanese Laid-Open Patent Publication Hei 2-062952).

The biosensor disclosed in this prior art is produced by the steps of forming an electrode system including a working electrode, a counter electrode and a reference electrode on an electrically insulating base plate using a screen printing method or the like and subsequently forming immediately above this electrode system an enzyme reaction layer including a hydrophilic polymer, an oxidoreductase and an electron acceptor.

When the biosensor thus produced is added with a drop of a sample solution containing a substrate over the enzyme reaction layer, dissolution of the enzyme reaction layer in the sample solution will occur, which triggers a reaction between the enzyme and the substrate (enzyme reaction). As a result, reduction of the electron acceptor will develop. Upon completion of this enzyme reaction, the reduced electron acceptor is reoxidized electrochemically. Based on the oxidation current value measured during this reoxidizing step, the concentration of the substrate in the sample solution can be quantitated.

The biosensor as described above permits measurements of various materials in principle if a suitable enzyme corresponding to the substrate of a target material is selected.

Enzymes, which contain protein as their main component, are normally present in dry state inside a biosensor. However, water contained in air may come in or out of the enzyme through its surface depending on the condition of temperature and humidity of air. Therefore, long contact of the enzyme with air will result in a change in water content which is present in the enzyme in a slight amount. As a result, the enzyme develops degeneration and loses its enzyme activity.

During preservation of a sensor after its production, when the activity of an enzyme contained in the sensor is impaired with time, the enzyme which should participate in enzyme reaction with a substrate is depleted. This produces a problem of incommensuration of the measured response current value with the substrate concentration.

In order to solve the above-mentioned problem, it is important to secure an environment which can retain enzyme activity for a long time in the vicinity of the enzyme.

It is also necessary to make smooth transfer of the substrate and electrons during enzyme reaction in order to increase sensor response.

BRIEF SUMMARY OF THE INVENTION

In view of the above-mentioned problem, the object of the present invention is to provide a biosensor with high stability against preservation by best reducing impairment of the activity of enzyme contained in the biosensor during its preservation after production.

Particularly, the present invention provides a compact disposable biosensor of low cost.

The present invention provides a biosensor comprising an electrically insulating base plate, an electrode system including at least a working electrode and a counter electrode formed on the base plate, and a reaction layer containing at least an enzyme and a sugar formed on the electrode system, wherein the enzyme is at least one selected from the group consisting of glucose oxidase, glucose dehydrogenase and fructose dehydrogenase and the sugar is at least one selected from the group consisting of trehalose, sucrose, glycerol, mannitol and ribose.

In a preferred mode of the present invention, the enzyme is glucose dehydrogenase whose coenzyme is pyrroloquinoline quinone and the sugar is trehalose.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
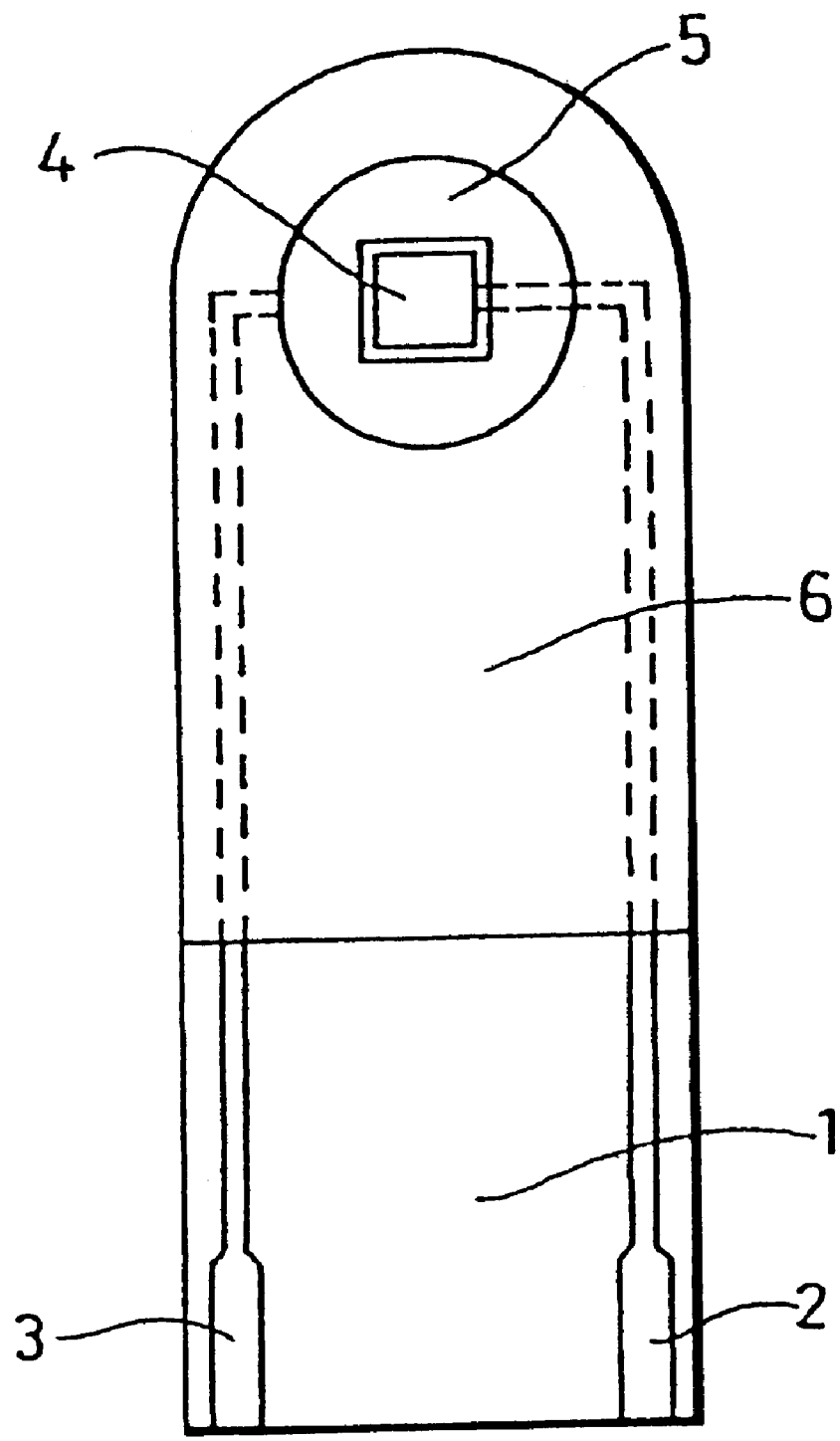
FIG. 1 is a schematic plan view of a biosensor in accordance with one example of the present invention with an omission of the reaction layer.

As noted above, the biosensor in accordance with the present invention contains a sugar in the reaction layer. When the reaction layer is formed by dropping an enzyme solution containing a sugar and drying the solution, the surface of the enzyme is coated with the sugar. This sugar coating protects the enzyme from any environmental changes such as temperature, humidity and so on and secures stability of the enzyme activity for a long time.

Furthermore, the sugar is readily dissolved in water. Therefore, it helps immediate dissolution of the reaction layer in a sample solution when the sample solution is added to the reaction layer. This is very convenient in order to proceed enzyme reaction and electrode reaction smoothly.

This effect can be expected from a variety of sugars. The biosensor in accordance with the present invention allows selection of various applicable enzymes.

When the enzyme is at least one selected from the group consisting of glucose oxidase, glucose dehydrogenase and fructose dehydrogenase, the presence of at least one sugar selected from the group consisting of trehalose, sucrose, glycerol, mannitol and ribose in the reaction layer is most preferable.

Particularly, when the enzyme is glucose dehydrogenase whose coenzyme is pyrrolo-quinoline quinone, selection of trehalose as the sugar produces a better sensor response even after the sensor is preserved for a long time, because trehalose has a surprising retaining effect of the activity of glucose dehydrogenase.

When the enzyme is glucose dehydrogenase whose coenzyme is pyrrolo-quinoline quinone and the sugar is trehalose, then it is appropriate to contain the enzyme glucose dehydrogenase 1 to 40 units and trehalose 4 to 400 nM (nanomole), more preferably 5 to 20 units and 40 to 200 nM, respectively, per sensor chip when the sensor is a disposable sensor which requires 3 to 4 µl blood as sample solution.

Applicable electron acceptors may be exemplified as ferricyanide ion, p-benzoquinone and its derivatives, phenazine methosulfate, methylene blue, ferrocene and its derivatives. The use of oxygen present in the sample solution as the electron acceptor can similarly produce a sensor response.

The biosensor in accordance with the present invention also permits further incorporation of a hydrophilic polymer in the reaction layer, in addition to the enzyme, sugar and electron acceptor.

The presence of such hydrophilic polymer in the reaction layer effectively prevents detachment or separation of the reaction layer from the surface of the electrode system. The hydrophilic polymer has another preventive effect against crack development on the surface of the reaction layer, which is effective to enhance the reliability of the resultant biosensor.

Preferred examples of the hydrophilic polymer for the above-mentioned purpose are carboxymethyl cellulose, hydroxyethyl cellulose, hydroxypropyl cellulose, methyl cellulose, ethyl cellulose, ethylhydroxyethyl cellulose, carboxymethylethyl cellulose, polyvinyl pyrrolidone, polyvinyl alcohol, polyamino acid such as polylysine, polystyrene sulfonate, gelatin and its derivatives, a polymer of acrylic acid or an acrylate, a polymer of methacrylic acid or a methacrylate, starch and its derivatives, a polymer of maleic anhydride or a maleate, agarose gel and its derivatives.

The reaction layer may be arranged in the biosensor in various ways in addition to its localization on the electrode system which is formed on the electrically insulating base plate. For example, it may be localized on other place than the electrode system on the base plate inside the biosensor. Otherwise, when a cover member is used which is to be combined with the base plate to form a sample solution supply pathway for supplying a sample solution to the electrode system between the cover member and the base plate, the reaction layer may be arranged on a side of the cover member which is exposed to the sample solution supply pathway formed between the cover member and the base plate.

In order to measure oxidation current, a two-electrode system including only a working electrode and a counter electrode and a three-electrode system further including a reference electrode in addition to the two electrodes may be used. The latter facilitates more precise measurements.

In the following, the present invention will be described more specifically referring to concrete examples.

FIG. 1 shows a schematic plan view of a biosensor in accordance with one example of the present invention from which the reaction layer has been removed. A silver paste is printed on an electrically insulating base plate 1 of polyethylene terephthalate by a known screen printing method so as to form leads 2 and 3 on the base plate 1. Subsequently, a conductive carbon paste containing a resin binder is printed on the base plate 1 so as to form a working electrode 4 thereon. The working electrode 4 is in contact with the lead 2. Then, an electrically insulating layer 6 is further formed on the base plate 1 by printing thereon an insulating paste. The electrically insulating layer 6 covers the periphery of the working electrode 4 so as to hold the exposed area of the working electrode 4 constant. Finally, the same carbon paste containing a resin binder as above is printed on the base plate 1 so as to make the carbon paste in contact with the previously formed lead 3 and a ring-like counter electrode 5 will result. In this way, an electrode system is formed on the base plate 1.

Figure 2:
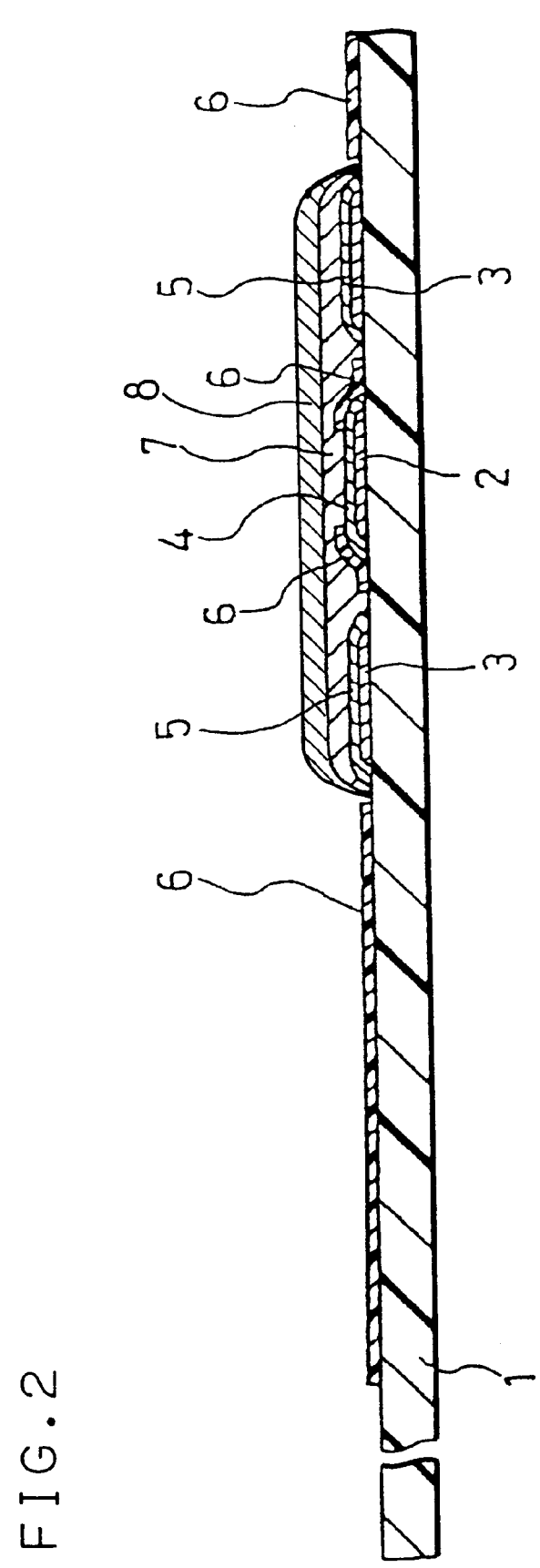
FIG. 2 is a longitudinal cross-sectional view of the vital parts of the biosensor of FIG. 1.

FIG. 2 is a longitudinal cross-sectional view of the biosensor of FIG. 1. On the electrode system formed in the manner as shown in FIG. 1, a reaction layer 8 containing at least an enzyme and a sugar in addition to a hydrophilic polymer 7 is further formed.

EXAMPLE 1

In this example, after the electrode system was formed on the base plate 1 as shown in FIG. 1, an aqueous 0.5 wt % sodium salt solution of a hydrophilic polymer carboxymethyl cellulose (hereinafter referred to as "CMC") was dropped on the electrode system and dried in a drier at 50° C. for 10 min to form a CMC layer 7 on the electrode system. Subsequently, on the CMC layer 7 thus formed, a mixed solution (4 µl) of 5000 units glucose dehydrogenase (hereinafter referred to as "GOD") whose coenzyme is pyrrolo-quinoline quinone (hereinafter referred to as "PQQ") as the enzyme, 20 µM trehalose as the sugar and 50 µM potassium ferricyanide as the electron acceptor dissolved in 1 ml water was dropped and dried to form a reaction layer 8 on the CMC layer. In this way, the biosensor of Example 1 was completed.

Separately, various aqueous glucose solutions were prepared as sample solutions by varying the glucose concentration. An aliquot of each of the sample solutions thus prepared was dropped on the reaction layer 8.

As noted above, upon supply of a sample solution containing glucose to the reaction layer, glucose in the sample solution is oxidized by the GDH contained in the reaction layer. In correspondence with this oxidation reaction, potassium ferricyanide in the reaction layer is reduced to potassium ferrocyanide.

One min after supply of the sample solution, a voltage of +0.5 V was applied onto the working electrode 4 using the counter electrode 5 as reference in order to reoxidize the potassium ferrocyanide. After 5 sec, the current flowing across the working electrode and the counter electrode was measured. In this way, current value was obtained from all the aqueous glucose solutions of different glucose concentrations and a response characteristic chart of the biosensor was prepared by plotting the glucose concentration on the horizontal axis and the current value on the vertical axis. The results are shown in FIG. 3.

Other biosensors were produced in the same manner as above and preserved for 6 months. A response characteristic chart was prepared for each biosensor in the above-mentioned manner. The results are also given in FIG. 3.

Figure 3:
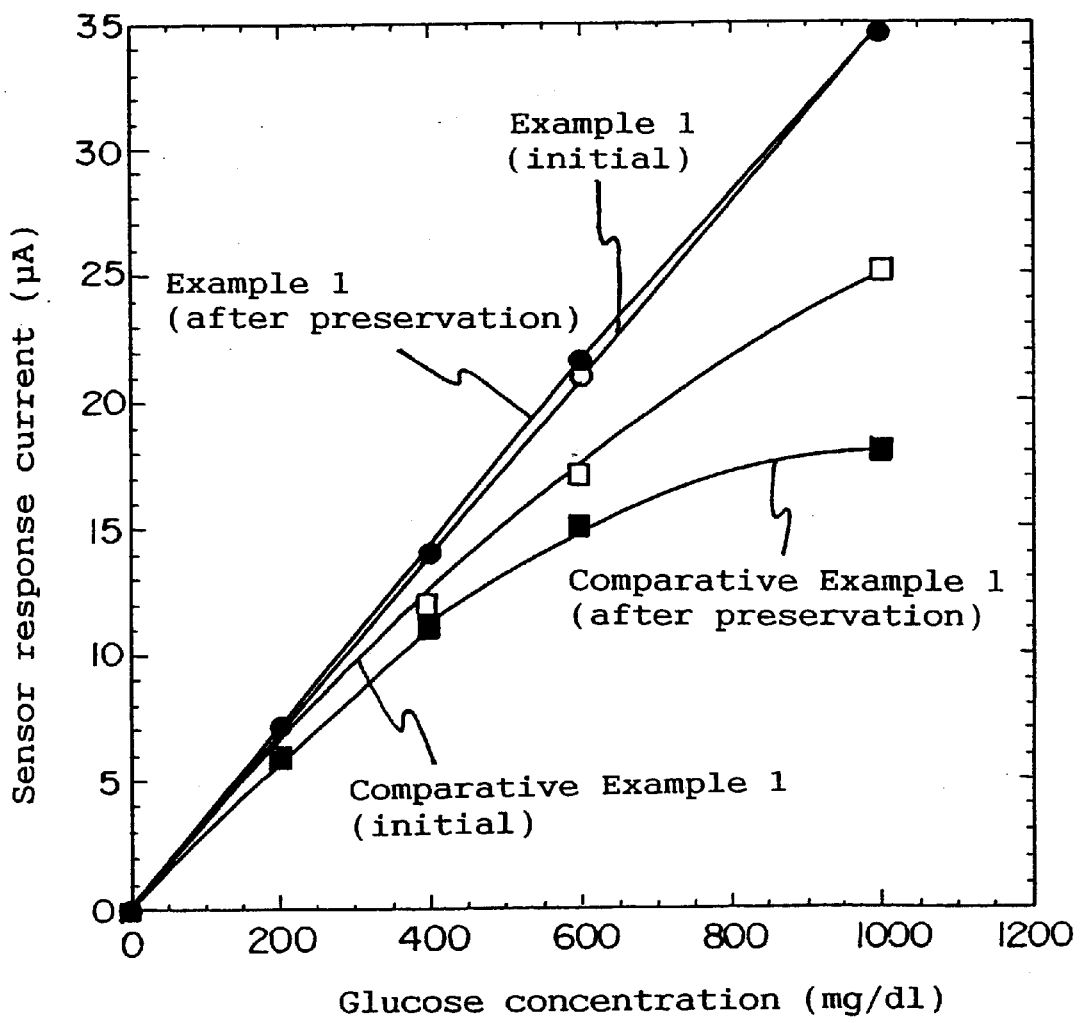
FIG. 3 is a graph showing the response characteristics of the biosensor in accordance with one example of the present invention and those of the biosensor of a comparative example.

As is evident from FIG. 3, a certain correlation exists between the glucose concentration and the current value; the correlation had sharp linearity. There was almost no change in the response of the biosensors immediately after production and after 6 months' preservation, demonstrating an excellent preservation characteristic of the biosensors.

Comparative Example 1

Another glucose biosensor was produced in the same manner as in Example 1, except for the absence of the sugar trehalose in the reaction layer 8. For comparison, a response characteristic chart of the biosensor was prepared in the same manner as in Example 1 immediately after production and after 6 months' preservation. The results are also shown in FIG. 3.

As is seen from FIG. 3, the biosensor of the comparative example produced a lower response current value than Example 1. After 6 months' preservation, the biosensor of the comparative example is decreased in the correlation between the glucose concentration and the current value, and is reduced in the response current value as compared to that immediately after production.

Figure 4:
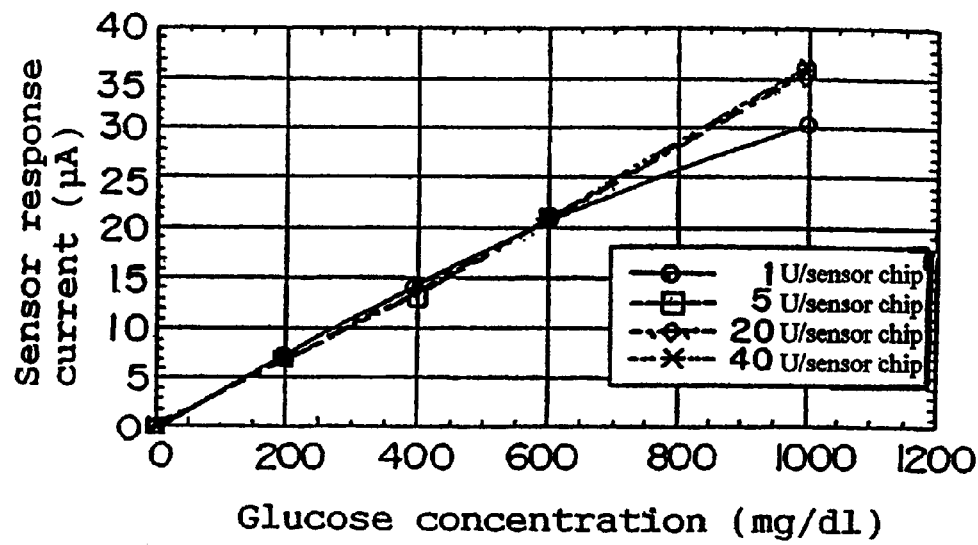
FIG. 4 is a graph showing the response characteristics of the sensors with different amounts of enzyme in the reaction layer.

Next, other biosensors were produced by adjusting the trehalose content in the reaction layer to a constant value (80 nM) and varying the content of GDH whose coenzyme is PQQ and preserved for 6 months. Then, the biosensors were examined for their response to the glucose concentration by supplying sample solutions of various glucose concentrations to the reaction layer. The results are shown in FIG. 4.

Figure 5:
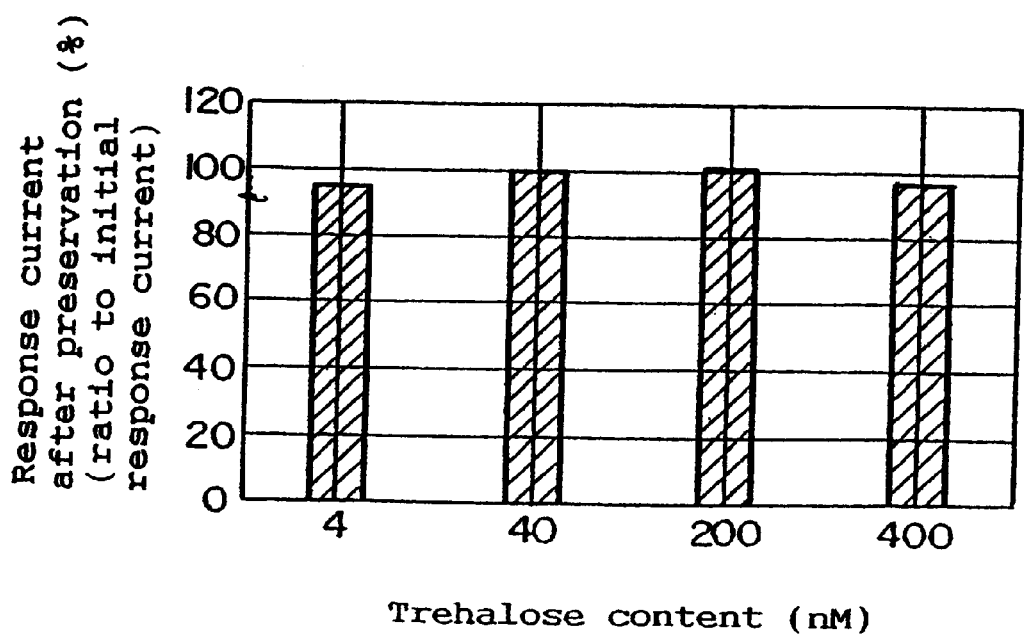
FIG. 5 is a graph showing a comparison of the ratio of the response current value after preservation to the initial response current value between various sensors with different amounts of trehalose in the reaction layer.

Other biosensors were also produced by adjusting the content of GDH whose coenzyme is PQQ to a constant value (20 units) and varying the content of trehalose from 4, 40, 200 to 400 nM. Then, the biosensors were examined for their response to the glucose concentration immediately after production and after 6 months' preservation by supplying a sample solution containing 10 mM (millimole) glucose. FIG. 5 shows the ratio of the response current value after 6 months' preservation to that immediately after production.

The results given in the figures indicate a linear correlation between the glucose concentration and the sensor response when the enzyme content is 1 unit and the glucose concentration is 600 mg/dl or less.

When the biosensor requires extremely excess enzyme contents of more than 40 units, such biosensor is disadvantageous from the aspect of production cost. Therefore, an appropriate enzyme content per sensor chip is 1 to 40 units and more preferably 5 to 20 units.

On the other hand, since the figure indicates that trehalose contents of 4 nM and 400 nM produced only slight impairment of the preservation characteristic of the resultant biosensors, preferable ranges of trehalose content per sensor chip are 4 nM to 400 nM and more preferable ranges are 40 nM to 200 nM.

EXAMPLE 2

In this example, a glucose biosensor was produced in the same manner as in Example 1, except for the use of glucose oxidase in place of GDH. Similar to Example 1, a response characteristic chart of the biosensor was prepared immediately after production and after 6 month's preservation.

The results showed a close correlation between the glucose concentration and the current value. Furthermore, there was almost no change in the response of the biosensor immediately after production and after 6 months' preservation, indicating a better preservation characteristic of the biosensor.

Comparative Example 2

For comparison, a glucose biosensor was produced in the same manner as in Example 2, except for the absence of trehalose in the reaction layer 8. Similar to Example 2, a response characteristic chart of the biosensor was also prepared immediately after production and after 6 month's preservation.

The results showed a lower response current value than that of Example 2. After 6 months' preservation, the biosensor was decreased in the correlation between the glucose concentration and the current value, and the response current value was also reduced as compared to that immediately after production.

EXAMPLE 3

In this example, a fructose biosensor was produced in the same manner as in Example 1, except for the use of fructose dehydrogenase in place of GDH.

Sample solutions of various fructose concentrations were prepared. With these various sample solutions, a response characteristic chart of the biosensor was prepared immediately after production and after 6 month's preservation in the same manner as in Example 1.

The results showed a close correlation between the fructose concentration and the current value. Furthermore, there was almost no change in the response of the biosensor immediately after production and after 6 months' preservation, indicating a better preservation characteristic of the biosensor.

Comparative Example 3

For comparison, a fructose biosensor was produced in the same manner as in Example 3, except for the absence of trehalose in the reaction layer 8. Similar to Example 3, a response characteristic chart of the biosensor was also prepared immediately after production and after 6 month's preservation.

The results showed a lower response current value than that of Example 3. After 6 months' preservation, the biosensor was decreased in the correlation between the fructose concentration and the current value, and the response current value was also reduced as compared to that immediately after production.

As discussed above, the present invention can provide a biosensor with an excellent long term preservation characteristic.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A biosensor comprising:

an electrically insulating base plate, an electrode system including at least a working electrode and a counter electrode formed on the base plate, and a reaction layer, wherein the reaction layer comprises trehalose and glucose dehydrogenase whose coenzyme is pyrrolo-quinoline quinone in a ratio of 40 to 200 nanomoles of trehalose to 5 to 20 units of glucose dehydrogenase whose coenzyme is pyrrolo-quinoline quinone, and an electron acceptor.

2. The biosensor of claim 1, wherein the reaction layer further comprises a polymer.

3. The biosensor of claim 2, wherein the polymer is selected from the group consisting of carboxymethyl cellulose, hydroxypropyl cellulose, methyl cellulose, ethyl cellulose, ethyl hydroxyethyl cellulose, carboxymethylethyl cellulose, polyvinyl pyrrolidone, polyvinyl alcohol, polyamino acids, polystyrene sulfonate, gelatin and its derivatives, polymers of acrylic acid, polymers of acrylate, polymers of methacrylic acid, polymers of methacrylate, starch and its derivatives, polymers of maleic anhydride, polymers of maleate, and agarose gel and its derivatives.

4. A biosensor comprising:
an electrically insulating base plate,
an electrode system including at least a working electrode and a counter electrode formed on the base plate, and
a reaction layer, wherein the reaction layer comprises trehalose and glucose dehydrogenase whose coenzyme is pyrrolo-quinoline quinone in a ratio of 2 to 40 nanomoles of trehalose per unit of glucose dehydrogenase whose coenzyme is pyrrolo-quinoline quinone, and an electron acceptor.

* * * * *